United States Patent [19]

Bäckerud

[11] 4,046,509
[45] Sept. 6, 1977

[54] METHOD FOR CHECKING AND REGULATING THE CONDITIONS OF CRYSTALLIZATION IN THE SOLIDIFICATION OF MELTS

[76] Inventor: Stig Lennart Bäckerud, Vallmovagen 3, Akersberga, Sweden

[21] Appl. No.: 666,582

[22] Filed: Mar. 15, 1976

Related U.S. Application Data

[63] Continuation of Ser. No. 137,260, April 26, 1971, abandoned.

[30] Foreign Application Priority Data

Apr. 28, 1970 Sweden .............................. 5755/70

[51] Int. Cl.² .................... G01N 31/00; G01N 33/00
[52] U.S. Cl. ................................. 23/230 A; 73/17 R; 156/601
[58] Field of Search ................... 156/601, 616, 616 A; 23/230 R, 253 R, 273 SP; 159/30; 73/17 R, 354, 64.1, 191; 23/230 A

[56] References Cited

U.S. PATENT DOCUMENTS

| 3,250,115 | 5/1966 | Donnell | 73/17 R |
| 3,375,106 | 3/1968 | McKissick et al. | 73/17 R |
| 3,546,921 | 12/1970 | Bourke et al. | 73/17 R |
| 3,670,558 | 6/1972 | Ryntz et al. | 73/17 R |
| 3,677,064 | 7/1972 | Simpson | 73/17 R |
| 3,681,972 | 8/1972 | Mahanty et al. | 73/17 R |
| 3,824,837 | 7/1974 | Nagaoka et al. | 73/17 R |

*Primary Examiner*—Frank W. Lutter
*Assistant Examiner*—Frank Sever
*Attorney, Agent, or Firm*—Stevens, Davis, Miller & Mosher

[57] ABSTRACT

A method for determining and regulating the conditions of crystallization in the solidification of melts. A sample of the melt is taken in a specially constructed test vessel with a volumetric capacity of from 5-50 cm³ and the temperature of the sample is measured centrally of the sample. From the information obtained a solidification curve is determined from which conditions characteristic of the solidification properties can be derived, thereby indicating the manner in which the melt should be modified to obtain desired properties.

4 Claims, 9 Drawing Figures

FIG. 4
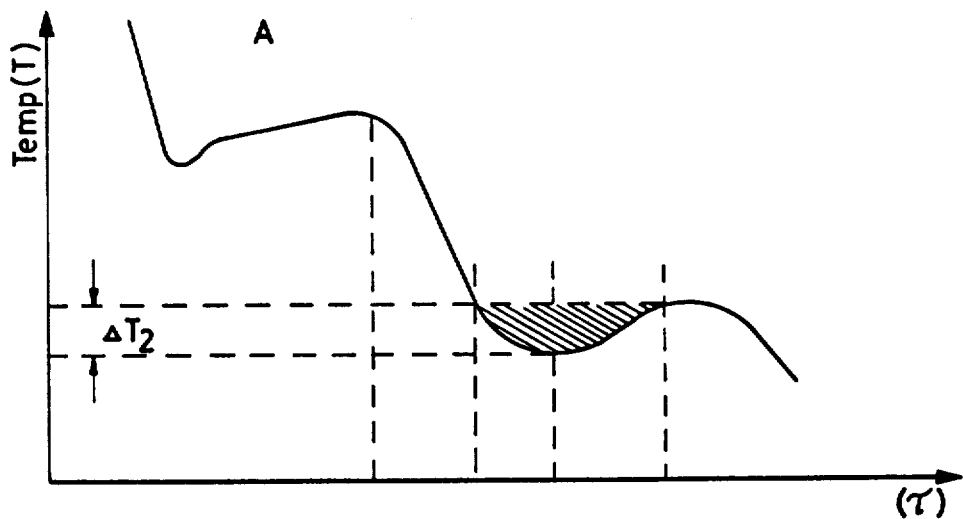
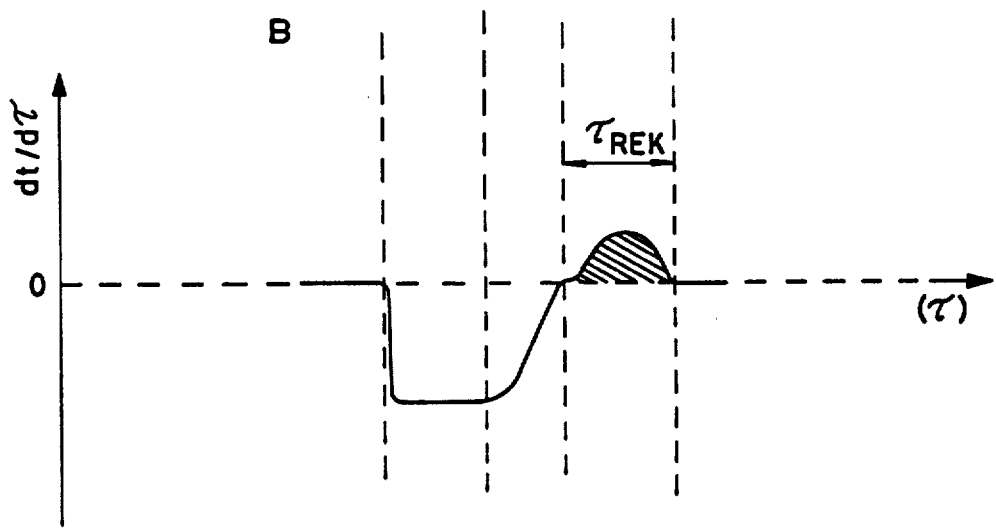
FIG. 5

METHOD FOR CHECKING AND REGULATING THE CONDITIONS OF CRYSTALLIZATION IN THE SOLIDIFICATION OF MELTS

This is a continuation of application Ser. No. 137,260 filed Apr. 26, 1971, now abandoned.

The present invention relates to a novel method for checking and regulating the conditions of crystallization in the solidification of melts. In principle, the method can be used in connection with all crystalline solidification processes, but has been particularly developed for the purpose of assessing and regulating the solidification of metal melts.

The properties of crystalline substances are mainly dependent on the physical processes occurring when the material passes from the liquid to the solid phase. In addition to such external factors as the construction of the mold, its heat transferring ability and the rate of solidification, the size, morphology, distribution and directionality of the formed crystals are dependent on the number of active nuclei, i.e. crystal grains present in the melt during the solidification process or located on those surfaces with which the melt comes into contact.

Normally, the number of active nuclei in newly manufactured metals is too small to provide for a homogeneous, fine-grain crystalline solidification. Consequently, it is often desired to stimulate nucleation by adding different substances or particles to the melt or to the casting equipment. The nucleation effect, however, is dependent on the physical and chemical condition of both the melt and the added substances.

An ordinary qualitative and quantitative chemical analysis of the melt, including the additives, will not therefore provide positive information on the actual nucleation effect attained during the solidification process, since the physical and chemical state of the melt does not only depend on the concentration of the different components. Consequently, when casting metallic materials it is normal practice to cast first a sample which after cooling is cut and prepared for examination, whereafter the obtained structure is studied by metallographical methods. This procedure, however, is time consuming and unavoidably reduces the production rate. Moreover, the properties of the melt can be changed during the time taken to carry out the tests, whereby the obtained result is no longer valid when the metal is cast.

With other casting methods, nucleation is suppressed instead of stimulated. Also in this instance, the inherent nucleation tendency of the melt is examined, by casting sample ingots.

By intensively studying the thermal conditions prevailing during nucleation and crystal growth, a method has been developed whereby the nucleation ability of a metal melt can be established from a sample taken from the melt within the course of a few minutes, whereafter, if necessary, the nucleation ability of the melt can be corrected in the desired manner. This applies to both primary and secondary nucleation, i.e. both the first solid phase formed from the melt and the elements or intermediary phases separated during the process of solidification.

The new method of the present invention for determining the conditions of crystallization in the solidification of melts, in which a sample is removed from the melt in a test vessel or transferred to a test vessel in which the sample is allowed to solidify simultaneously as the change in temperature with time is registered by a temperature sensing means, is mainly characterized by the steps of establishing the course of solidification curve during the crystal growth for the melt in question and comparing the course of the curve with a corresponding curve obtained under similar test conditions for a melt of substances having substantially the same composition as the test melt and with known crystallization conditions.

Thermal analysis for determining the chemical composition of a melt is a method long known to the art. The method is founded on the assumption that phase transformations occur at constant temperature and assumes that the solidification curve (i.e. the relationship between time and temperature during the process of solidification) presents horizontal plateau where growth of the solid phase takes place. These temperatures are read off on appropriate instruments, and a measurement of the composition of the melt is obtained from an equilibrium-phase diagram. The method is suited for analysing binary alloy systems, although some success has also been had in correcting obtained measuring values for the influence of a third element.

A close study of the solidification process, however, shows that the solid phase formed in a melt does not grow at a constant temperature unless the heat transport from the melt is infinitely slow. New and important information concerning the nucleation and growth conditions of the solid phase can thus be obtained by measuring temperature changes in connection with phase transformations: since the whole solidification process takes place during a limited period of time, i.e. within the course of a few minutes. To enable such changes to be measured, however, the solidification process must take place under carefully controlled conditions. Above all, it should be seen that:

I. it must be possible for the transfer of heat from the melt being studied to take place at a controllable rate, which can be reproduced from one measuring process to the other, II. the temperature of the sample mold in which the measurement is taken has initially a temperature in excess of the nucleation temperature of the melt, III. convections in the sample melt during the solidification process are reduced to a minimum by appropriate means, e.g. magnetic means, IV. the dissipation of heat during solidification of the sample takes place substantially uniformly in all directions, so that those crystals formed on the walls of the mold during the growth process fully encapsulate a residual melt in the centre of the mold, where a temperature sensing device, for example a thermocouple, is located, V. the material from which the sample mold and the thermocouple are made and the protective tubing around the thermocouple can not react with the melt or act as a relatively effective nucleant for the metal melt, and that the heat conductive properties of the material allow the necessary relatively rapid solidification process to take place.

If the above conditions are fulfilled and a solidification curve is thus recorded, the information given by the curve is such that it is possible to establish within a very short time, either manually or automatically, whether the measured value deviates from the desired values, and to correct any deviation which might be discovered. Deviations from desired values can, of course, be corrected by any known means, such as the addition of known grain refining substances, or by decanting or filtering surplus quantities of grain refining substances from the melt.

The conditions for assessing the recorded measurement values will now be discussed with reference to the accompanying drawings, in which:

FIG. 4 illustrates a solidification curve showing secondary crystal growth for an aluminum-silicon alloy without the addition of nucleating particles;

FIG. 5 illustrates the derivative dT/dr of the curve of FIG. 4;

1. PRIMARY OR SINGLE PHASE CRYSTAL GROWTH WITH DIFFERENT QUANTITIES OF NUCLEANTS

Figure 1:
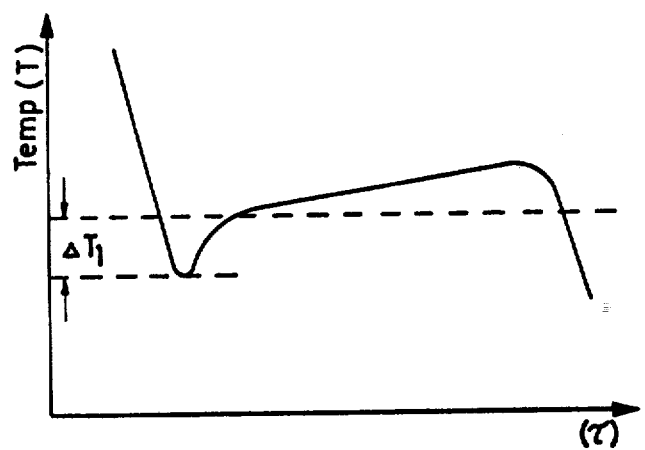
FIG. 1 illustrates a solidification curve for aluminum metal without the addition of nucleating particles.

The first section of a solidification curve measured in accordance with the aforementioned conditions obtains for a melt of pure aluminium having a commercial purity (Al 99.7%) the principle course illustrated in FIG. 1. Although aluminium has been selected to illustrate the invention, it will be understood that the invention can be applied to the majority of melts.

The reason for the increase in temperature during the so-called plateau phase is to be found in the fact that the growth rate of the crystals decreases from the surface of the sample mold in towards the centre and that the growth temperature is consequently increased. The test was carried out in a ceramic crucible having a volumetric capacity of approximately 40 cm³ and in the centre of which was placed a thermoelement. Prior to recording the desired information, the test vessel was completely submerged in molten pure aluminium and filled with a portion of the melt, at the same time obtaining the temperature of the melt.

The structure of pure aluminium corresponding to FIG. 1 is almost completely formed of a few, long columnar crystals extending from the periphery in towards the centre of the sample. The solid phase has thus only nucleated at the walls of the mold at a degree of under cooling which is corresponded in FIG. 1 by the value $\Delta T_1$.

Figure 2:
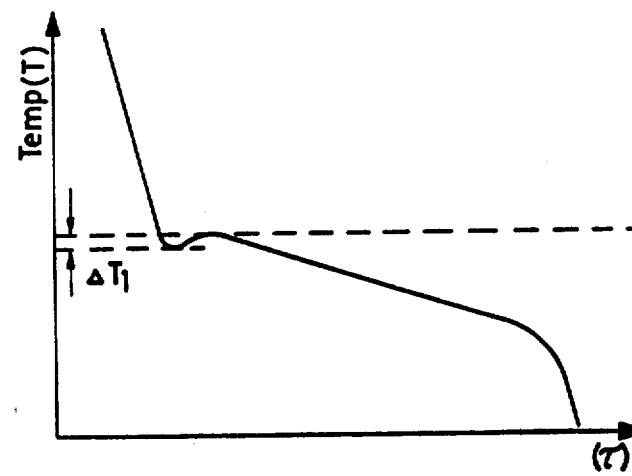
FIG. 2 illustrates a solidification curve for aluminum metal with the addition of an effective amount of nucleating particles.

FIG. 2 illustrates a solidification curve drawn on the same base metal as that of FIG. 1, but with the addition of effective nucleating particles.

The remarkable differences between the two solidification curves reside firstly in the value of the requisite degree of undercooling ($\Delta T_1$) for the nucleation and secondly in the slope of the plateau.

When the nucleant is really effective, the required degree of undercooling will be small, since nuclei are formed throughout the whole sample. A network of solid phases is developed very early in this process and creates solid contact between the thermocouple and the walls of the test vessel. This dendritic network obtains a purer composition than the remainder of the melt and during the subsequent solidification process more enriched phases will solidify in the inter-dendritic regions. Subsequent to the residual melt having been enriched in this manner, the growth temperature will constantly decrease (microsegregation effect).

Figure 3:
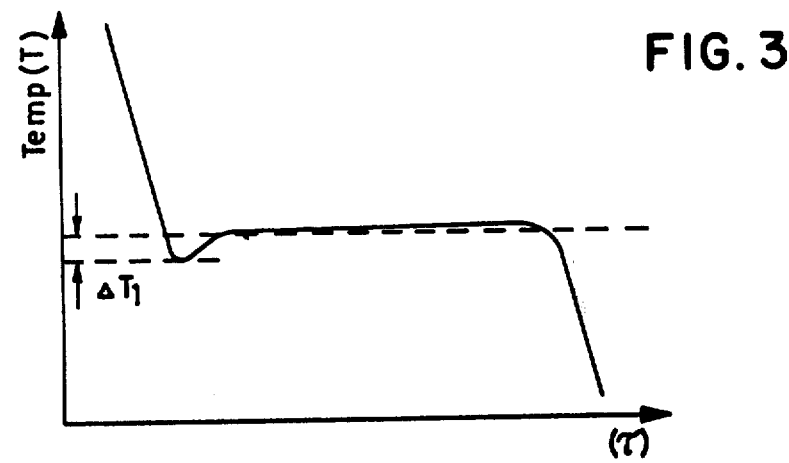
FIG. 3 illustrates a solidification curve for aluminum metal with the addition of an insufficient amount of nucleating particles.

FIG. 3 illustrates a solidification curve for pure aluminium to which nucleating agents have been added in an insufficient quantity or which provide an insufficient effect.

The original degree of undercooling ($\Delta T_1$) is, in this instance, greater than in the former instance. Moreover, the plateau has a slight upward inclination. This indicates that the formed nuclei have been unable to form a continuous network throughout the volume of the sample, but that the growth, as in FIG. 1, is controlled by the growth of dendrites from the surface of the mold in towards the centre thereof.

It will be apparent from the foregoing that effective nucleation with primary crystal growth is characterized by a negative value on the temperature/time derivative ($dT/dr<0$) during the plateau phase, i.e. that the curve during the plateau phase shows a falling temperature. It is also evident that the undercooling becomes smaller the more effective the crystal formation is.

2. SECONDARY OF MULTI-PHASE CRYSTAL GROWTH

To illustrate the conditions with secondary crystal growth, FIGS. 4 and 5 show solidification curves of an unmodified and a modified hypoeutectic aluminium-silicon cast alloy, the derivative $dT/dr$ for these solidification curves also being shown.

Formation of the primary $\alpha_{Al}$-phase is analogous with the aforegoing description of the primary crystal growth. Of interest in FIGS. 4 and 5 is the temperature sequence with the secondary phase formation. In Al-Si-casting alloys, the eutectic reaction comprises a coupled growth of silicon and aluminium phase. Difficulties exist, however, in nucleating the silicon phase and it requires only a few silicon particles to grow in the inter-dentritic inter spaces in order for the total eutectic growth rate to be low.

A strong undercooling ($\Delta T_2$) and a slow increase in the eutectic growth temperature (recalescence) is the result. It has been found that the area under the derivated solidification curve or the time from the beginning of the nucleation period to the complete recalescence provides a quantitative measurement which corresponds to the structure image.

By adding different substances to the melt (for example sodium) it is possible to stimulate nucleation of the silicon phase, and therewith also the growth conditions for the eutectic phases. This results in a lower degree of undercooling and a more rapid recalescence, i.e. the area under the derivative and the time for recalescence become small in comparison with the condition of unmodified material.

MULTI-PHASE CRYSTAL GROWTH WITH THE SECONDARY PHASE IN DIFFERENT CRYSTAL FORMS

Figure 6:
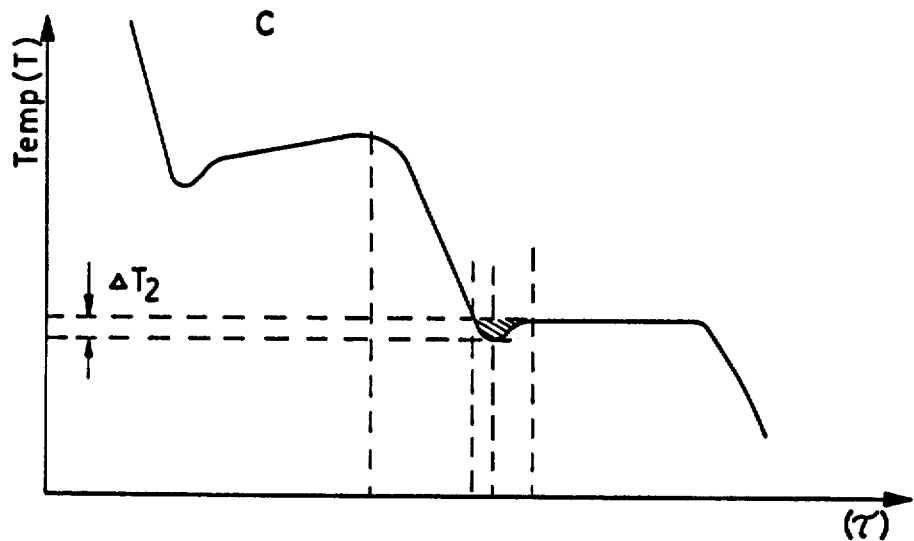
FIG. 6 illustrates a solidification curve showing secondary crystal growth for an aluminum-silicon alloy with the addition of an effective amount of nucleating particles.
Figure 7:
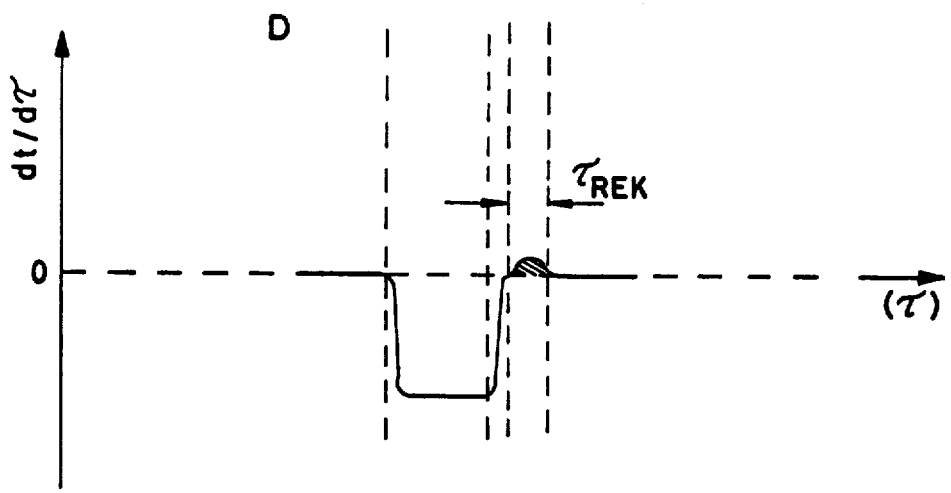
FIG. 7 illustrates the derivative dT/dr of the curve of FIG. 6.
Figure 8:
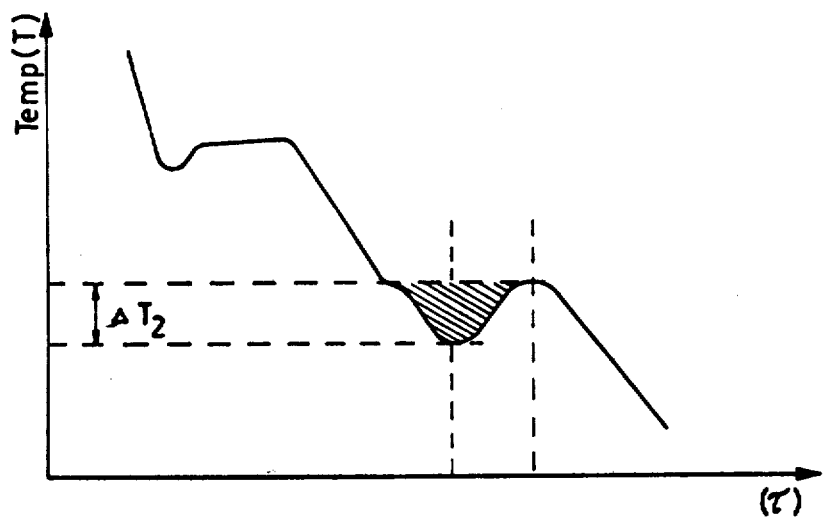
FIG. 8 illustrates a solidification curve showing multiphase crystal growth for cast iron.
Figure 9:
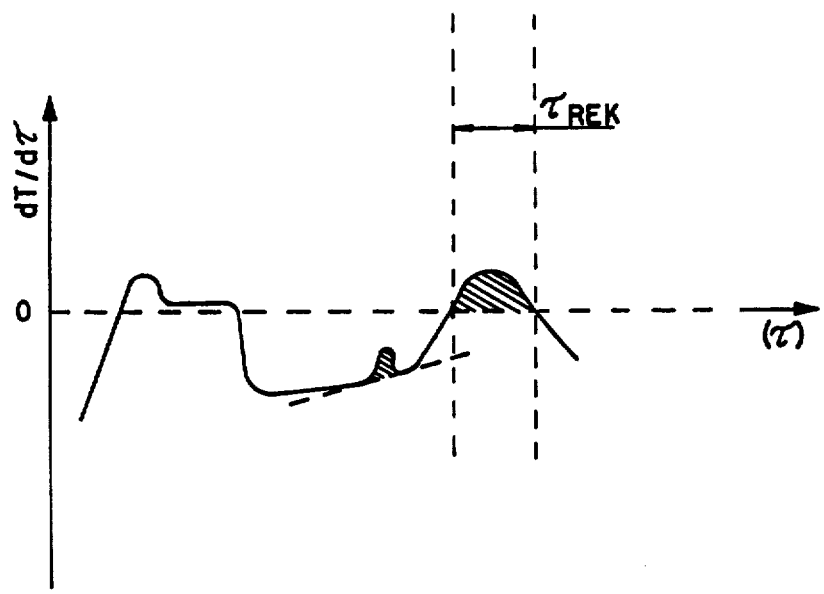
FIG. 9 illustrates the derivative dT/dr of the curve of FIG. 8.

To illustrate the utility of the method for assessing secondary properties, FIG. 6 illustrates a curve for the solidification of cast iron. The curve has, in principle, the same course as the previous curves, and is based on aluminium and aluminium alloys. At the beginning of the solidification of the eutectic phase there is obtained in the solidification curve and inflection point which manifests itself as a maximum on the derivative. It has been found that this peak is directly related to the quantity of graphite which is precipitated as flaky crystals, the subsequent undercooling and recalescence disclosing the nodular graphite precipitation. Thus, the method of the present invention is extremely useful in assessing and regulating the precipitation of graphite in cast iron.

As previously mentioned, the test is carried out in a test vessel which must fulfill given conditions on the rate of heat transfer from the sample, the temperature of the sample vessel at the beginning of the measuring process, the convections in the melt, the geometric shape of the test cavity and the inertness of the walls of the test vessel with regard to nucleation. The metal from which the test vessel is made is determined by the nature of the metal melt to be tested. When measuring the crystal formation conditions in an aluminium melt, graphite crucibles can be used to advantage, while measurements made on cast iron require ceramic crucibles.

The volume of test material can very within wide limits, but should suitably lie between 5–50 cm$^3$ and the temperature should be measured at preferably not less than 1 cm from the walls of the test vessel. Once having knowledge of the basic principle of the present invention, however, it should be quite within the scope of one skilled in the art to determine experimentally suitable measuring conditions so that reproduceable values are obtained.

The aforedescribed equipment for sampling metal melts should suitably be provided with recording instruments (suitably a highly sensitive two-channel tracing device, means for suppressing zero point, and derivating and integrating devices) for measuring and recording:

1. Undercooling prior to primary nucleation
2. "the average plateau temperature" for chemical analysis of the melt
3. the slope of plateaux in the solidification curve, i.e. the derivative $dT/dr$
4. secondary undercooling and delayed recalescence, optionally with the assistance of a derivative and/or integrator unit.

One of the advantages afforded by the derivation process is that the derivator can be easily set to zero in the middle of the measuring area of the recording instrument. Possible drift in the thermocouple or changes in content areas for different materials do not therefore affect the position of the signal along the recording scale.

I claim:

1. A method for checking and regulating the crystallization conditions in the solidification of a melt comprising
   a. transferring a sample from the melt to a test vessel maintained at a uniform temperature greater than the nucleation temperature of the melt with the melt having a volume of 5 to 50 cm$^3$ and a vessel heat conductivity such that the sample after removal from the melt will solidify in a period of time from 5 seconds to 5 minutes in said vessel,
   b. measuring the change in temperature with time with temperature sensing means in said test vessel,
   c. recording said change with recording means, to form a temperature-time solidification curve,
   d. comparing at least one of the following characteristic conditions in the recorded temperature-time solidification curve with a corresponding temperature-time solidification curve obtained by the solidification of a melt with known crystallization conditions of morphology and size and substantially the same chemical composition, viz.,
      1. the slope of the temperature-time solidification curve at the primary plateau temperature,
      2. the area under positive values of the derivative of the solidification curve at multi-phase eutectic solidification,
   e. analyzing said corresponding solidification curve and at least one of the characteristic conditions to determine deviations and
   f. correcting said melt from which the sample is taken if (e) reveals an unacceptable deviation from said corresponding solidification curve.

2. The method of claim 1, wherein said test vessel is immersed in the melt, filled with melt and removed therefrom at a uniform temperature.

3. The method of claim 2, wherein said sample is taken in a quantity of from 5 - 50 cm$^3$ and measuring the temperature centrally of the sample at a distance of at least 1 cm from the walls of the sample vessel by means of a thermo-element.

4. The process of claim 1, wherein said melt is cast iron treated for nodularization of graphite in which case the graphite morphology can be determined by measuring the positive values of the derivative of the temperature-time curve measured during the solidification process as obtained before the main eutectic reaction takes place.

* * * * *